(12) United States Patent
Aduri et al.

(10) Patent No.: US 9,120,809 B2
(45) Date of Patent: Sep. 1, 2015

(54) PROCESS FOR PREPARING ALDITOL ACETALS

(71) Applicant: RELIANCE INDUSTRIES LIMITED, Mumbai, Maharashtra (IN)

(72) Inventors: Pavankumar Aduri, Maharashtra (IN); Parasu Veera Uppara, Maharashtra (IN); Mangesh Sakhalkar, Maharashtra (IN); Uday Ratnaparkhi, Maharashtra (IN)

(73) Assignee: RELIANCE INDUSTRIES LIMITED, Mumbai (IN)

( * ) Notice: Subject to any disclaimer, the term of this patent is extended or adjusted under 35 U.S.C. 154(b) by 165 days.

(21) Appl. No.: 13/936,413

(22) Filed: Jul. 8, 2013

(65) Prior Publication Data
US 2013/0303787 A1  Nov. 14, 2013

Related U.S. Application Data

(63) Continuation of application No. PCT/IN2011/000121, filed on Feb. 28, 2011.

(30) Foreign Application Priority Data

Jan. 10, 2011 (IN) .............................. 79/MUM/2011

(51) Int. Cl.
C07D 493/04 (2006.01)
(52) U.S. Cl.
CPC .................................. C07D 493/04 (2013.01)
(58) Field of Classification Search
CPC ...................................................... C07D 493/04
See application file for complete search history.

(56) References Cited

U.S. PATENT DOCUMENTS

| | | | |
|---|---|---|---|
| 3,721,682 A | 3/1973 | Murai et al. | |
| 4,267,110 A | 5/1981 | Uchiyama | |
| 4,429,140 A | 1/1984 | Murai et al. | |
| 4,562,265 A | 12/1985 | Machell | |
| 4,902,807 A | 2/1990 | Kobayashi et al. | |
| 5,023,354 A | 6/1991 | Salome et al. | |
| 5,104,840 A | 4/1992 | Chauvin et al. | |
| 5,731,474 A | 3/1998 | Scrivens et al. | |
| 5,892,124 A | 4/1999 | Olivier et al. | |
| 6,500,964 B2 | 12/2002 | Lever et al. | |
| 6,527,977 B2 | 3/2003 | Helber et al. | |
| 6,573,405 B1 | 6/2003 | Abbott et al. | |
| 7,183,433 B2 | 2/2007 | Abbott et al. | |
| 7,196,221 B2 | 3/2007 | Abbott et al. | |
| 2005/0147889 A1 | 7/2005 | Ohzuku et al. | |
| 2006/0183654 A1 | 8/2006 | Small | |
| 2008/0307703 A1 | 12/2008 | Dietenberger et al. | |
| 2009/0247432 A1 | 10/2009 | Miller | |

FOREIGN PATENT DOCUMENTS

| | | |
|---|---|---|
| CN | 1858048 A | 11/2006 |
| CN | 1903857 A | 1/2008 |
| CN | 101440025 A | 5/2009 |
| CN | 101544628 A | 9/2009 |
| CN | 101723852 A | 6/2010 |
| WO | 0226701 A2 | 4/2002 |
| WO | 2006044187 A1 | 4/2006 |

OTHER PUBLICATIONS

International Search Report of PCT/IN2011/000121, mailed Oct. 20, 2011, 3 pages.
Angew. Chem. Int. Ed., Ionic Liquids—New "Solutions" for Transition Metal Catalysis, 2000, 39, 3772-3789.
Olivier-Bourbigou, H., et al., Applied Catalysis A: General, 373, 1-56, 2010.
Deetlefs, M., et al., Liquid Structure of the Ionic Liquid 1,3-Dimethylimidazolium, J. Physical Chemistry B. 110, 12055-12061, 2006.
Canongia Lopez, J. N. and Padua, A. A. H., Nanostructural Organization in Ionic Liquids, J. Physical Chemistry B. 110, 3330-3335, 2006.

*Primary Examiner* — Sun Jae Yoo
(74) *Attorney, Agent, or Firm* — Collard & Roe, P.C.

(57) ABSTRACT

A process for preparing alditol Acetals via a dehydrocondensation reaction is disclosed. The reaction is carried out by adding an aldehyde and an aldiol using a metal salt based ionic liquid as an acid catalyst. The ionic liquid used in the process is prepared by dissolving a hydrogen donor and a compound providing counter ion in a solvent.

12 Claims, No Drawings

PROCESS FOR PREPARING ALDITOL ACETALS

CROSS REFERENCE TO RELATED APPLICATIONS

This application is a continuation of PCT/IN2011/000121 filed on 28 Feb. 2011, which claims priority under 35 U.S.C. §119 of 79/MUM/2011 filed on Jan. 10, 2011, the disclosures of which are incorporated by reference. The international application under PCT article 21(2) was published in English.

FIELD OF INVENTION

This invention relates to a method of producing alditol acetals in an ionic fluid.

BACKGROUND OF THE INVENTION

The acetal compound is the reaction product of an alditol and benzaldehyde. Alditol acetals, such as 1,3:2,4-bis(4-methylbenzylidene) sorbitol (MDBS) and 1,3:2,4-bis(3,4-dimethylbenzylidene) sorbitol (DMDBS) derivative compounds are known compounds which find their utility as an additive in polypropylene. Acetals of substituted and unsubstituted aldehydes are also known to be useful as nucleating agents, gelling agents, processing aids, and strength modifiers in polyolefin resins, polyester resins, deodorant, and antiperspirant compositions; hydrocarbon fuels and paints.

Acetal alditols are typically prepared by the condensation reaction of an aromatic aldehyde with an alditol containing 6 carbon atoms like sorbitol. For MDBS and DMDBS structures, such reactions involve two moles of the aldehyde and one mole of an alditol.

Several methods for the preparation of acetal-alditols have been reported in U.S. Pat. No. 4,267,110, U.S. Pat. No. 3,721,682, U.S. Pat. No. 4,429,140; U.S. Pat. No. 4,562,265; U.S. Pat. No. 4,902,807; U.S. Pat. No. 5,023,354; U.S. Pat. No. 5,731,474 and U.S. Pat. No. 6,500,964.

The hitherto reported methods suffer from several shortcomings. Majority of the earlier known processes employ various organic solvents which necessitates high temperature for carrying out the reaction thereby increasing the cost component. Furthermore, most of solvents are very expensive and they too render the process un-economical.

Attempts have been made in the past to overcome the above mentioned shortcomings by employing the acidic catalyst for improving the yield and the versatility (ability to employs variety of substituted aldehydes) the process.

The presently known processes for the preparation of acetals which employ acidic catalysts still suffer from several limitations. Though mineral acids serve as good catalysts for the acetalization process, they are very corrosive in nature. Furthermore, the final product resulting from such processes needs to be purified by neutralizing the residual free acid. Though the yields offered by all teachings are acceptable for the practical purposes, all the methods are not effective from the perspective of versatility, environmentally friendliness, energy efficient, reliability, cost-effective, and safe production.

Ionic systems, which are examples of viscous molten salts, have a number of interesting and useful properties, and have utility, for example, as highly polar solvents, co-solvents and catalyst in synthetic chemistry. They also have been found to be useful in applications in various fields such as electrochemistry, synthesis of chemical compounds, dyes, batteries, fuel cells, photovoltaic devices, electro-deposition processes, semi conductor cleaning, pyrolysis, gasification, in applications involving cellulose dissolution, for the electroplating of metals as described, for example in U.S. Pat. No. 6,573,405, U.S. Pat. No. 7,183,433, U.S. Pat. No. 7,196,221, US Patent Appl. No. 2005/0147889, U.S. Pat. No. 6,527,977, US Patent Appl. No. 2008/0307703, US Patent Appl. No. 2006/0183654, US Patent Appl. No. 2009/0247432.

Ionic compounds/liquids exhibit very low or no vapour pressure and thus, in contrast to many conventional molecular solvents produce virtually no vapours. They are therefore advantageous from a health, safety and environmental point of view.

Processes for preparation of acetals and di-acetals other than MDBS and DMDBS structures using ionic liquids as catalysts and/or reaction medium have been reported. For example, CN 101440025 discloses a method for preparation of ethylidene ether or ketal which employs N-methyl glyoxaline bisulphate ionic liquid catalyst. Other patents which disclose the use of ionic liquid as catalyst for preparation of acetals other than MDBS and DMDBS structures include CN 101723852, CN 101544628 and CN 1858048.

None of the hitherto reported processes for preparation of MDBS and DMDBS have employed ionic compounds/liquids as catalysts and/or reaction medium. There exists a need for process for preparation of MDBS and DMDBS which uses ionic compounds/liquids as the catalyst and or reaction medium. There also remains a need for a process for preparation of acetals, particularly MDBS and DMDBS which does not employ any expensive solvents and corrosive mineral acids.

DEFINITIONS

As used in the present specification, the following words and phrases are generally intended to have the meanings as set forth below, except to the extent that the context in which they are used indicates otherwise.

The phrase "ionic fluid" is used herein to refer to the solvate prepared whereby ionic compound formed in-situ by dissolving the mixture of a hydrogen donor selected from the group consisting of methanesulfonic acid (MSA), para toluenesulfonic acid (PTSA), oxalic acid, citric acid, benzoic acid, maleic acid and tartaric acid and a 'counter ion providing compound' selected from the group consisting of a metal salts such as sodium chloride and zinc chloride.

OBJECTS OF THE INVENTION

It is an object of the present invention to provide a process for preparation of alditol acetal derivative compounds in high yields and purity.

It is another object of the present invention to provide a process that allows the preparation of symmetrical and asymmetrical dibenzylidene sorbitol compounds without any limitation.

It is still another object of the present invention to provide a process for preparation of acetal derivatives which is economical.

It is yet another object of the present invention to provide a process for preparation of acetal derivatives which is environment friendly.

It is yet another object of the present invention to provide a process for preparation of acetal derivatives wherein there the final product is devoid of any residual free acid.

It is yet another object of the present invention to provide a process for preparation of acetal derivatives which is safe.

It is a further object of the invention to provide a method which allows the production of monoacetal and diacetal derivatives without the formation of triacetal derivates.

SUMMARY OF INVENTION

In accordance with the present invention there is provided a process for preparation of acetal derivatives selected from the group consisting of 1,3:2,4-bis(4-methylbenzylidene) sorbitol (MDBS) and 1,3:2,4-bis(3,4-dimethylbenzylidene) sorbitol (DMDBS) comprising the following steps:
preparing a metal salt based ionic fluid containing an in situ formed ionic compound by dissolving a hydrogen donor and a counter ion providing compound in a solvent;
carrying out the dehydrocondensation reaction by adding an aldehyde and an alditol in a mole ratio of 2:1 in the ionic fluid under continuous stirring to form a reaction mixture;
stirring the resultant reaction mixture to maintain the contents in a suspension form; and
discontinuing the stirring of the reaction mixture to allow the mass formed in the reaction mixture to settle;
isolating and purifying the mass by subjecting the reaction mixture to filtration, to obtain a mother liquor containing the ionic fluid, unconverted reactants and the solid mass;
washing and drying the solid mass to obtain an acetal derivative without any free acid residue present therein.

Typically, in accordance with the process of the present invention, the ionic fluid acts as an acid catalyst as well as a reaction medium for the dehydrocondensation reaction.

Typically, the ionic fluid is prepared by mixing the equimolar quantities of the hydrogen donor and the counter ion providing compound in the solvent.

Typically, the solvent is at least one selected from the group of carboxylic acids, amides, alcohols, amines, ketones (aldehydes), asters, alkyl halides, ethers, aromatics for example; methanol, ethanol, propan-1-ol, propan-2-ol, 1-butanol, isobutanol, 2-butanol, tert-butanol, dichloromethane, tetrahydrofuran, methyl acetate, ethyl acetate, acetone, dimethylformamide, acetonitrile, dimethyl sulfoxide, formic acid, acetic acid, methyl ethyl ketone, dimethyl carbonate, diethyl ketone, acetic anhydride, acetone, tert-butyl methyl ether, diethyl amine, diethylene glycol, N,N-dimethylacetamide, diethylene glycol dimethyl ether, ethylene glycol dimethyl ether, ethylene glycol, glycerin, hexamethylphosphor amide, hexamethylphosphorous triamide, isoamyl alcohol, 2-methoxyethanol, 2-methoxyethyl acetate, 1-methyl-2-pyrrolidinone, nitromethane, propanoic acid, pyridine, hydrogen fluoride, hydrogen chloride, and water.

In a second aspect of the present invention, there is provided a process for preparation of acetal derivatives selected from the group consisting of 1,3:2,4-bis(4-methylbenzylidene) sorbitol (MDBS) and 1,3:2,4-bis(3,4-dimethylbenzylidene) sorbitol (DMDBS) comprising the following steps:
preparing a metal salt based ionic liquid by heating a hydrogen donor and a counter ion providing compound;
carrying out the dehydrocondensation reaction by adding an aldehyde and an alditol in a mole ratio of 2:1 in the ionic liquid under continuous stirring to form a reaction mixture;
stirring the resultant reaction mixture to maintain the contents in a suspension form; and
discontinuing the stirring of the reaction mixture to allow the mass formed in the reaction mixture to settle;
isolating and purifying the mass by subjecting the reaction mixture to filtration, to obtain a mother liquor containing the ionic liquid, unconverted reactants and the solid mass;
washing and drying the solid mass to obtain an acetal derivative without any free acid residue present therein.

Typically, the ionic liquid acts as a catalyst and a reaction medium.

Typically, the hydrogen donor is selected from the group consisting of methanesulfonic acid (MSA), para toluenesulfonic acid (PTSA), oxalic acid, citric acid, benzoic acid, maleic acid and tartaric acid.

Typically, the counter ion providing compound is selected from the group consisting of sodium chloride and zinc chloride.

Typically, the aldehyde is at least one aldehyde selected from the group of aldehydes consisting of unsubstituted benzaldehyde, and substituted aldehydes including benzaldehyde, 4-methylbenzaldehyde, 3-methylbenzaldehyde, 4-propylbenz aldehyde, p-ethylbenz aldehyde, 4-butylbenzaldehyde, 4-Isopropylbenzaldehyde, 4-isobutylbenzaldehyde, 2,4-dimethylbenzaldehyde, 3,4-dimethylbenzaldehyde, 3,5-dimethylbenz aldehyde, 3-methyl-4-methoxybenzaldehyde, 2,4,5-trimethylbenzaldehyde, 3-hex-1-ynylbenzaldehyde, piperonal, 3-hydroxy-5,6,7,8-tetrahydro-2-naphthaldehyde, 3-Methoxy-5,6,7,8-tetrahydro-2-naphthaldehyde, 3-Hydroxy-8-isopropyl-5-methyl-2-naphthaldehyde, 2-naphthaldehyde, 3-methoxybenzaldehyde, 4-methoxybenzaldehyde, 3,4-dimethoxybenzaldehyde, 3-ethoxybenzaldehyde, 4-ethoxybenzaldehyde, 3,4-diethoxybenzaldehyde, 4-allyloxybenzaldehyde, 4-propoxybenzaldehyde, 4-carboxybenzaldehyde, 3-bromobenzaldehyde, 4-bromobenzaldehyde, 2-chlorobenzaldehyde, 3-chlorobenzaldehyde, 4-chlorobenzaldehyde, 3-fluorobenzaldehyde, 4-fluorobenzaldehyde, 3,4-dichlorobenzaldehyde, 3,5-dichlorobenzaldehyde, 3,5-dibromobenzaldehyde, 3,5-difluorobenzaldehyde, 4-chloro-3-fluorobenzaldehyde, 3-bromo-4-fluorobenzaldehyde, 4-fluoro-3-methyl-, 5,6,7,8-tetrahydro-2-naphthaldehyde, 4-fluoro-3,5-dimethylbenzaldehyde, 4-(trifluoromethyl)benzaldehyde, 3-bromo-4-ethoxybenzaldehyde and mixtures thereof.

Typically, the alditol is selected from the group consisting of sorbitol (100%), or iso-propyl sorbitol. Alternatively, the alditol is an aqueous solution of sorbitol with a concentration in the range of about 40% to about 99%.

Typically, the method step of stirring is carried out for a period in the range of about 5 to 8 hours.

Typically, the mother liquor is recycled in the method step of dehydrocondensation at least 35 times, preferable 30 times.

DESCRIPTION OF THE INVENTION

In order to overcome the shortcomings of the hitherto reported processes which employ expensive solvents or corrosive mineral acid catalysts for the preparation of acetals, the inventors of the present invention have chosen the specific ionic fluids for the preparation of the acetals, particularly DMDBS and MDBS.

Accordingly, in a first aspect of the present invention there is provided a process for preparation of acetal derivatives particularly, DMDBS and MDBS by dehydrocondensation reaction between an aldehyde and alditol using a metal salt based ionic fluid which serves the dual role of a reaction catalyst and a reaction medium, comprising the following steps:

preparing an ionic fluid containing an in situ formed ionic compound by dissolving a hydrogen donor and a counter ion providing compound in a solvent;

carrying out the dehydrocondensation reaction by adding an aldehyde and an alditol in a mole ratio of 2:1 in the ionic fluid under continuous stirring to form a reaction mixture;

stirring the resultant reaction mixture to maintain the contents in a suspension form; and discontinuing the stirring of the reaction mixture to allow the mass formed in the reaction mixture to settle;

isolating and purifying the mass by subjecting the reaction mixture to filtration, to obtain a mother liquor containing the ionic fluid, unconverted reactants and the solid mass;

washing and drying the solid mass to obtain an acetal derivative without any free acid residue present therein.

The ionic fluid comprises an 'in situ formed' ionic compound formed from the hydrogen bonding between a hydrogen donor and a counter ion which catalyses the dehydrocondensation. Besides, it also serves as a reaction medium for carrying out the reaction. Typically, the method step of preparing an ionic fluid comprises adding a hydrogen donor and a counter ion providing compound independently in equimolar quantities to a solvent leading to the in-situ formation of an ionic compound in the solvent.

The energy requirement for the process for preparation of an ionic fluid in accordance with the present invention is very low and it can be carried out at room temperature also.

The solvent employed for preparation of the ionic fluid in accordance with the present invention is selected from the group consisting of carboxylic acids, amides, alcohols, amines, ketones (aldehydes), asters, alkyl halides, ethers, aromatics for example; methanol, ethanol, propan-1-ol, propan-2-ol, 1-butanol, isobutanol, 2-butanol, tert-butanol, dichloromethane, tetrahydrofuran, methyl acetate, ethyl acetate, acetone, dimethylformamide, acetonitrile, dimethyl sulfoxide, formic acid, acetic acid, methyl ethyl ketone, dimethyl carbonate, diethyl ketone, acetic anhydride, acetone, tert-butyl methyl ether, diethyl amine, diethylene glycol, N,N-dimethylacetamide, diethylene glycol dimethyl ether, ethylene glycol dimethyl ether, ethylene glycol, glycerin, hexamethylphosphor amide, hexamethylphosphorous triamide, isoamyl alcohol, 2-methoxyethanol, 2-methoxyethyl acetate, 1-methyl-2-pyrrolidinone, nitromethane, propanoic acid, pyridine, hydrogen fluoride, hydrogen chloride, and water.

Typically, in accordance with the process of the present invention, the ionic fluid acts as an acid catalyst as well as a reaction medium for the dehydrocondensation reaction.

In a second aspect of the present invention, there is provided a process for preparation of acetal derivatives selected from the group consisting of 1,3:2,4-bis(4-methylbenzylidene) sorbitol (MDBS) and 1,3:2,4-bis(3,4-dimethylbenzylidene) sorbitol (DMDBS) comprising the following steps:

preparing a metal salt based ionic liquid by heating a hydrogen donor and a counter ion providing compound;

carrying out the dehydrocondensation reaction by adding an aldehyde and an alditol in a mole ratio of 2:1 in the ionic liquid under continuous stirring to form a reaction mixture;

stirring the resultant reaction mixture to maintain the contents in a suspension form; and discontinuing the stirring of the reaction mixture to allow the mass formed in the reaction mixture to settle;

isolating and purifying the mass by subjecting the reaction mixture to filtration, to obtain a mother liquor containing the ionic liquid, unconverted reactants and the solid mass;

washing and drying the solid mass to obtain an acetal derivative without any free acid residue present therein.

Typically, the ionic liquid acts as a catalyst and a reaction medium.

Typically, the hydrogen donor is selected from the group consisting of at least one acid selected from the group consisting of methanesulfonic acid (MSA), para toluenesulfonic acid (PTSA), oxalic acid, citric acid, benzoic acid, maleic acid and tartaric acid. The Catalytic activity was found to be decreasing with decrease in hydrogen donor capability of an acid. The catalytic activity in the wide range of temperatures depends on the salt that is forming ionic compound with hydrogen bond donor indicating the stability and strength of the hydrogen bond (Angew. Chem. Int. Ed., 2000, 39, 3772-3789, Ionic Liquids—New "Solutions" for Transition Metal Catalysis).

Strength and stability of the hydrogen bond also depends on the solubility of the salts in solvents and water-solvent systems.

Typically, the counter ion providing compound is selected from the group consisting of sodium chloride and zinc chloride. In a preferred embodiment, the counter ion providing compound is sodium chloride.

The counterion providing compounds provide counter ion that are capable of forming a hydrogen bond in solvent or aqueous-solvent mixture. The ionic compound formation by result of cations and anions connection by hydrogen bond were reported to have supramolecular structural organization (Olivier-Bourbigou, H., et al., Applied Catalysis A: General, 373, 1-56, 2010; Deetlefs, M., et al., J. Physical Chemistry B. 110, 12055-12061, 2006; Canongia Lopez, J. N. and Padua, A. A. H., J. Physical Chemistry B. 110, 3330-3335, 2006). The continuous microdomains structure formed due to the network of hydrogen bond seem to be favorable for catalytic reactions since acid is not available in free form and this will not impart any residual acidity to the final product.

The aldehyde employed in the process of the present invention is at least one selected from the group consisting of unsubstituted benzaldehyde, and substituted aldehydes including benzaldehyde, 4-methylbenzaldehyde, 3-methylbenzaldehyde, 4-propylbenzaldehyde, p-ethylbenzaldehyde, 4-butylbenzaldehyde, 4-Isopropylbenzaldehyde, 4-isobutylbenzaldehyde, 2,4-dimethylbenzaldehyde, 3,4-dimethylbenzaldehyde, 3,5-dimethylbenzaldehyde, 3-methyl-4-methoxybenzaldehyde, 2,4,5-trimethylbenzaldehyde, 3-hex-1-ynylbenzaldehyde, piperonal, 3-hydroxy-5,6,7,8-tetrahydro-2-naphthaldehyde, 3-Methoxy-5,6,7,8-tetrahydro-2-naphthaldehyde, 3-Hydroxy-8-isopropyl-5-methyl-2-naphthaldehyde, 2-naphthaldehyde, 3-methoxybenzaldehyde, 4-methoxybenzaldehyde, 3,4-dimethoxybenzaldehyde, 3-ethoxybenzaldehyde, 4-ethoxybenzaldehyde, 3,4-diethoxybenzaldehyde, 4-allyloxybenzaldehyde, 4-propoxybenzaldehyde, 4-carboxybenzaldehyde, 3-bromobenzaldehyde, 4-bromobenzaldehyde, 2-chlorobenzaldehyde, 3-chlorobenzaldehyde, 4-chlorobenzaldehyde, 3-fluorobenzaldehyde, 4-fluorobenzaldehyde, 3,4-dichlorobenzaldehyde, 3,5-dichlorobenzaldehyde, 3,5-dibromobenzaldehyde, 3,5-difluorobenzaldehyde, 4-chloro-3-fluorobenzaldehyde, 3-bromo-4-fluorobenzaldehyde, 4-fluoro-3-methyl-,5,6,7,8-tetrahydro-2-naphthaldehyde, 4-fluoro-3,5-dimethylbenzaldehyde, 4-(trifluoromethyl)benzaldehyde, 3-bromo-4-ethoxybenzaldehyde and mixtures thereof.

Typically, the alditol used in accordance with the process of the present invention is selected from the group consisting of iso-propyl sorbitiol, and sorbitol (100%). Alternatively, an aqueous solution of sorbitol with a concentration in the range of about 40% to about 99% is used as the alditol or iso-propyl sorbitol.

Typically, the dehydrocondensation reaction is carried out at a temperature with a range of about 25° C. to about 50° C. Typically, the method step of stirring is carried out for a period in the range of about 5 to 10 hours. Typically, the mother liquor containing the ionic fluid along with unconverted reactants is recycled in the method step of dehydrocondensation reaction. Typically, the mother liquor is recycled at least 35 times, preferably 30 times without the loss of catalytic activity of the ionic fluid.

The inventors of the present invention have surprisingly found out that the product obtained by the process of the present invention remains completely free of any residual free acid. This obviates the need for neutralization of the reaction mixture before isolation of the product as is required in the known processes. The residual free acid in the product is highly undesirable since it promotes the hydrolysis of the end product at high temperature, especially during the drying process.

The process of the present invention is therefore particularly advantageous since it obviates the need for neutralizing residual free acid in the end product thereby reducing the cost and complexity of the process. This demonstrates the utility of the ionic fluids as a reaction medium to carry out the acid based dehydrocondensation reactions.

The following examples further illustrate the present invention, but are not be construed as limiting the invention as defined in the claims appended hereto.

Example: 1

Toluene-4-sulphonic acid monohydrate (PTSA), a hydrogen donor (2 gms) was mixed with sodium chloride (0.6 gms) in equal mole ratio and 30 ml methanol was added to the salt mixture and stirred well to prepare ionic fluid. The ionic fluid obtained was used for carrying out the dehydration reaction at 26° C. 3,4 dimethyl benzaldehyde and sorbitol in 2:1 mole ratio were added to the ionic compound and stirred to initiate the reaction. The solid mass formed within few minutes of starting the reaction. The stirring speed was increased to keep the mass in suspension condition and reaction was continued for 5 hrs. The solid product was filtered to obtain mother liquor and a white solid mass. The white solid mass was washed with 120 ml methanol. The white solid product was dried in oven at 95° C. for 2 hrs followed by air dried for 4 hrs for measuring the yield. The yield was found to be 77%.

Example: 2

The procedure of example 1 was followed except 70% aqueous solution of sorbitol (1.5 ml) was replaced with 100% sorbitol. The yield was found to be 75%.

Example: 3

The procedure of example 1 was followed except, PTSA was replaced with oxalic acid (1.3 gm) and 1.2 gm NaCl with 1:2 mole ratio. Reaction was carried out for 8 hrs. The yield was found to be 75%.

Example: 4-7

Example for Recycling/Reusing of Mother Liquor

The procedure of example 1 was followed except, the mother liquor obtained from fresh cycle was replenished with 3,4 dimethyl benzaldehyde and sorbitol and continued the reaction. The details of the reactions are given in Table 1.

| Cycle No | Ratio of Sorbitol to Aldehyde | Methanol (ml) | Ratio of NaCl to PTSA | Reaction Time (Hours) | Yield, % |
|---|---|---|---|---|---|
| Fresh | 1:2 | 165 | 1:1 | 5.5 | 77 |
| Cycle 1 | 1:2 | — | — | 5.5 | 86 |
| Cycle 2 | 1:2 | — | — | 5.5 | 90 |
| Cycle 3 | 1:2 | — | — | 5.5 | 95 |

Test Data

Comparative Example

The process for preparing dibenzylidene sorbitol by a prior art process as disclosed in U.S. Pat. No. 4,429,140 was carried out to comparatively asses the energy requirement, time requirement and the overall complexity of the process in terms of the number of reagents used in the process in accordance with the present invention.

3,4 dimethyl benzaldehyde and sorbitol in 2.5:1 mole ratio were mixed in cyclohexane (100 weight parts) and methanol (100 weight parts mixed). To this mixture 98% sulfuric acid (0.5 weight parts) serving as catalyst was added and the dehydrocondensation reaction was carried out at 78 to 82° C. in the nitrogen atmosphere for 3 hours. The water formed during the reaction was continuously distilled off as an azeotropic mixture along with cyclohexane and methanol. The cyclohexane condensed and separated off by the condenser, was recycled through the reaction system, while aqueous layer was withdrawn from the system. The reaction was completed after 3 hours cooled, neutralized with an aqueous KOH solution, washed with hot water and filtered to obtain white powder. Yield was 95% and purity was 97.5%.

It was found that the process in accordance of the present invention required less energy since it was carried out at room temperature. Furthermore, the process of the present invention also involved less number of method steps which did not require any of the harmful or corrosive chemical like sulfuric acid. Still furthermore, unlike the prior art process described herein above, the catalyst in the form of ionic fluid in case of the process of the present invention was recyclable thereby making the process environment friendly.

While certain embodiments of the inventions have been described, these embodiments have been presented by way of example only, and are not intended to limit the scope of the inventions. Variations or modifications to the design and construction of this invention, within the scope of the invention, may occur to those skilled in the art upon reviewing the disclosure herein. Such variations or modifications are well within the spirit of this invention. The accompanying claims and their equivalents are intended to cover such forms or modifications as would fall within the scope and spirit of the invention.

The numerical values given for various physical parameters, dimensions and quantities are only approximate values and it is envisaged that the values higher than the numerical value assigned to the physical parameters, dimensions and quantities fall within the scope of the invention and the claims unless there is a statement in the specification to the contrary.

The invention claimed is:

1. A process for preparation of acetal derivatives selected from the group consisting of 1,3:2,4-bis(4-methylbenzylidene) sorbitol (MDBS) and 1,3:2,4-bis(3,4-dimethylbenzylidene) sorbitol (DMDBS) comprising the following steps:
   a. preparing a metal salt based ionic fluid containing an in situ formed ionic compound by dissolving a hydrogen donor and a counter ion providing compound in a solvent;
   b. carrying out a dehydrocondensation reaction by adding an aldehyde and an alditol in a mole ratio of 2:1 in the ionic fluid under continuous stirring to form a reaction mixture;
   stirring the resultant reaction mixture to maintain the contents in a suspension form;
   d. discontinuing the stirring of the reaction mixture to allow the mass formed in the reaction mixture to settle;
   e. isolating and purifying the mass by subjecting the reaction mixture to filtration, to obtain a mother liquor containing the ionic fluid, unconverted reactants and a solid mass; and
   f. washing and drying the solid mass to obtain an acetal derivative without any free acid residue present therein.

2. The process as claimed in claim 1, wherein the ionic fluid acts as an acid catalyst for the dehydrocondensation reaction.

3. The process as claimed in claim 1, wherein the ionic fluid acts as a reaction medium for the dehydrocondensation reaction.

4. The process as claimed in claim 1, wherein the metal salt based ionic fluid is prepared by mixing the equimolar quantities of the hydrogen donor and the counter ion providing compound in the solvent.

5. The process as claimed in claim 1, wherein the solvent is at least one selected from the group consisting methanol, ethanol, propan-1-ol, propan-2-ol, 1-butanol, isobutanol, 2-butanol, tert-butanol, dichloromethane, tetrahydrofuran, methyl acetate, ethyl acetate, acetone, dimethylformamide, acetonitrile, dimethyl sulfoxide, formic acid, acetic acid, methyl ethyl ketone, dimethyl carbonate, diethyl ketone, acetic anhydride, tert butyl methyl ether, diethyl amine, diethylene glycol, N,N-dimethylacetamide, diethylene glycol dimethyl ether, ethylene glycol dimethyl ether, ethylene glycol, glycerin, hexamethylphosphor amide, hexamethylphosphorous triamide, isoamyl alcohol, 2-methoxyethanol, 2-methoxyethyl acetate, 1-methyl-2-pyrrolidinone, nitromethane, propanoic acid, pyridine, hydrogen fluoride, hydrogen chloride, and water.

6. The process as claimed in claim 1, wherein the hydrogen donor is selected from the group consisting of PTSA (Paratoluenesulfonic acid) and oxalic acid.

7. The process as claimed in claim 1, wherein the counter ion providing compound is selected from the group consisting of sodium chloride and zinc chloride.

8. The process as claimed in claim 1, wherein the aldehyde is at least one aldehyde selected from the group consisting of 4-methylbenzaldehyde and 4-dimethylbenzaldehyde.

9. The process as claimed in claim 1, wherein the alditol is sorbitol.

10. The process as claimed in claim 1, wherein the alditol is an aqueous solution of sorbitol with a concentration in the range of 40% to 99%.

11. The process as claimed in claim 1, wherein the method step of stirring is carried out for a period in the range of 5 to 8 hours.

12. The process as claimed claim 1, wherein the mother liquor is recycled in the method step of dehydrocondensation at least 35 times.

* * * * *